US009045438B2

(12) United States Patent
Lara Ochoa

(10) Patent No.: US 9,045,438 B2
(45) Date of Patent: Jun. 2, 2015

(54) PHARMACEUTICAL COMPOSITION CONTAINING GLIMEPIRIDE AND METFORMIN HYDROCHLORIDE

(75) Inventor: Jose Manuel Francisco Lara Ochoa, Mexico City (MX)

(73) Assignee: Silanes S.A. de C.V., Col. del Valle (MX)

( * ) Notice: Subject to any disclaimer, the term of this patent is extended or adjusted under 35 U.S.C. 154(b) by 1055 days.

(21) Appl. No.: 10/502,403

(22) PCT Filed: Jan. 25, 2002

(86) PCT No.: PCT/MX02/00003
§ 371 (c)(1),
(2), (4) Date: Jun. 20, 2005

(87) PCT Pub. No.: WO03/061643
PCT Pub. Date: Jul. 31, 2003

(65) Prior Publication Data
US 2005/0239887 A1 Oct. 27, 2005

(51) Int. Cl.
*C07D 241/24* (2006.01)
*A61K 31/155* (2006.01)
*A61K 31/64* (2006.01)
*C07D 207/277* (2006.01)
*A61K 31/205* (2006.01)

(52) U.S. Cl.
CPC ............ *C07D 241/24* (2013.01); *A61K 31/155* (2013.01); *A61K 31/64* (2013.01); *C07D 207/277* (2013.01)

(58) Field of Classification Search
None
See application file for complete search history.

(56) References Cited

U.S. PATENT DOCUMENTS

| 3,072,527 | A | | 1/1963 | Cohen | |
| 5,416,105 | A | | 5/1995 | Satoh et al. | |
| 5,955,106 | A | * | 9/1999 | Moeckel et al. | 424/464 |
| 6,011,049 | A | * | 1/2000 | Whitcomb | 514/369 |
| 6,031,004 | A | * | 2/2000 | Timmins et al. | 514/635 |
| 6,303,146 | B1 | | 10/2001 | Bonhomme et al. | |
| 6,348,469 | B1 | | 2/2002 | Seth | |
| 6,499,984 | B1 | * | 12/2002 | Ghebre-Sellassie et al. | 425/135 |
| 6,559,188 | B1 | * | 5/2003 | Gatlin et al. | 514/641 |
| 6,682,759 | B2 | | 1/2004 | Lim et al. | |
| 6,890,957 | B2 | * | 5/2005 | Chandran et al. | 514/634 |
| 2003/0187074 | A1 | | 10/2003 | Hussain et al. | |
| 2004/0219212 | A1 | | 11/2004 | Castan et al. | |
| 2007/0264331 | A1 | | 11/2007 | Regalado et al. | |

FOREIGN PATENT DOCUMENTS

| WO | WO 97/17975 A1 | 5/1997 |
| WO | WO 00/40233 A1 | 7/2000 |
| WO | WO 01/32158 A2 | 5/2001 |
| WO | WO 03/061643 A1 | 7/2003 |
| WO | WO 2004/045622 A1 | 6/2004 |

OTHER PUBLICATIONS

Seymour. Glyburide/Metformin HCL Clinical Review In: Diabetes Intervention: Achieving tight glycemic control through combination therapy. Managed Care (Special Supplement). 2001; 10(2):1-24, especially pp. 11-16.*
Mccall. Clinical review of glimepiride. Expert Opinion on Pharmacotherapy. 2001;2(4):699-713.*
Abbink, E.J., et al., "Vascular effects of glibenclamide vs. glimepiride and metformin in Type 2 diabetic patients," *Diabet. Med.* 19:136-143, Blackwell Science (Feb. 2002).
Bressler, R., and Johnson, D.G., "Pharmacological Regulation of Blood Glucose Levels in Non-Insulin-Dependent Diabetes Mellitus," *Arch. Intern. Med.* 157:836-848, American Medical Association (1997).
Cefalu, W.T., et al., "Insulin Sensitivity is Improved After Glipizide GITS Mono-Therapy and in Combination with Metformin," *Diabetologia* 39:A231, Springer Verlag (1996).
Cefalu, W.T., et al., "Combination Glipizide GITS/Metformin Normalizes Glucose and Improves Insulin Sensitivity in Hyperinsulinemic Moderately Well Controlled NIDDM," *Diabetes* 45:201A, American Diabetes Association (1996).
Charpentier, G., at al., "Improved glycaemic control by addition of glimepiride to metformin monotherapy in Type 2 diabetic patients," *Diabet. Med.* 18:828-834, Blackwell Science (Oct. 2001).
Crouse III, J.R., et al., "Effects of Combination Glipizide GITS/Metformin Treatment on Oxidizability of LDL in Non-Insulin Dependent Diabetes Mellitus," *Circulation* 94:I-508, Lippincott Williams & Wilkins (1996).
Dagogo-Jack, S., and Santiago, J.V., "Pathophysiology of Type 2 Diabetes and Modes of Action of Therapeutic Interventions," *Arch. Intern. Med.* 157:1802-1817, American Medical Association (1997).
Defronzo, R.A., "Pharmacologic Therapy for Type 2 Diabetes Mellitus," *Ann. Intern. Med.* 131:281-303, American College of Physicians (1999).
Defronzo, R.A,, et al., "Efficacy of Metformin in Patients with Non-Insulin-Dependent Diabetes Mellitus," *N. Engl. J. Med.* 333:541-549, Massachusetts Medical Society (1995).
Garber, A.J., et al., "Efficacy of Metformin in Type II Diabetes: Results of a Double-Blind, Placebo-controlled, Dose-Response Trial," *Am. J. Med.* 102:491-497, Excerpta Medica, Inc. (1997).

(Continued)

*Primary Examiner* — Trevor Love
(74) *Attorney, Agent, or Firm* — Sterne, Kessler, Goldstein & Fox P.L.L.C.

(57) ABSTRACT

Pharmaceutical compositions of the active substances glimepiride with metformin or its salts such as hydrochloride, succinate, fumarate, etc. are useful to control blood glucose in patients with type 2 diabetes. To prove the effectiveness of the combination, clinical studies were conducted that demonstrated the existence of not only an additive effect, but also a synergistic effect of the two drugs compared with monotherapy using only one of the drugs used in combination. In consequence, the combination may be used as an effective and safe therapy to control blood glucose in patients with type 2 diabetes, using different proportions of the active substances in combinations suitable for the needs of different patients.

19 Claims, No Drawings

(56) References Cited

OTHER PUBLICATIONS

González-Oritz, M., et al., "Eficacia y seguridad de la terapia hipoglucemiante oral combinada de glimepirida más metformina en una sola forma farmacéutica en pacientes con diabetes mellitus tipo 2 y falla secundaria a monoterapia con glibenclamida," *Rev. Invest. Clin.* 56:327-333, Instituto Nacional de la Nutrición (May-Jun. 2004).

English Language Translation of González-Oritz, M., et al., "Efficacy and safety of glimepiride plus metformin in a single presentation, as combined therapy, in patients with type 2 diabetes mellitus and secondary failure to glibenclamide, as monotherapy," *Rev. Invest. Clin.* 56:327-333, Instituto Nacional de la Nutrición (May-Jun. 2004).

González-Oritz, M., et al., "Efficacy of glimepiride/metformin combination versus glibenclamide/metformin in patients with uncontrolled type 2 diabetes mellitus," *J. Diabetes Complicat.*, Elsevier Science Publishing Company, 4 pages, Article in Press, uncorrected proof (Sep. 2008).

Gomis, R., et al., "Appropriate Timing of Glimepiride Administration in Patients with Type 2 Diabetes Millitus," *Endocrine 13*:117-121, Endocrine Society (2000).

Hermann, L.S., et al., "Therapeutic Comparison of Metformin and Sulfonylurea, Alone and in Various Combinations," *Diabetes Care 17*:1100-1109, American Diabetes Association (1994).

Higginbotham, L. and Martin, F.I.R., "Double-Blind Trial of Metformin in the Therapy of Non-Ketotic Diabetics," *Med. J. Aust.* 2:154-156, Australian Medical Publishing Company Limited (1979).

Holstein, A., et al., "Lower Incidence of Severe Hypoglycaemia in Type 2 Diabetic Patients Treated with Glimepiride Versus Glibenclamide," *Diabetologia 43*:A 40, Springer Verlag (2000).

Müller, G., et al., "Differential interaction of glimepiride and glibenclamide with the β-cell sulfonylurea receptor," *Biochim. Biophys. Acta 1191*:267-277, Elsevier Pub. Co. (1994).

Rosenstock, J., et al., "Glimepiride, a New Once-Daily Sulfonylurea," *Diabetes Care 19*:1194-1199, American Diabetes Association (1996).

Sato, J., et al., "Comparison between effects of glimepiride and glibenclamide on in vivo insulin action," in *Proceedings of the Fourth International Symposium on Treatment of Diabetes Mellitus, Nagoya*, Oct. 26-27, 1993, Sakamoto, N., et al., eds., Excerpta Medica, Amsterdam, Netherlands, pp. 341-348 (1994).

Scheen, A.J., and Lefèbvre, P.J., "Oral Antidiabetic Agents. A Guide to Selection," *Drugs 55*:225-236, ADIS Press (1998).

Sifton, D., ed., "Anzemet® Injection," in *Physicians Desk Reference, 54th Ed.*, Medical Economics Company, Montvale, NJ, pp. 1349-1352 (2000).

Sonnenberg, G.E., et al., "Short-Term Comparison of Once- Versus Twice-Daily Administration of Glimepiride in Patients with Non-Insulin-Dependent Diabetes Mellitus," *Ann. Pharmacother.* 31:671-676, Harvey Whitney Books Company (1997).

Vigneri, R., et al., "Treatment of NIDDM Patients with Secondary Failure to Glyburide: Comparison of the Addition of Either Metformin or Bed-Time NPH Insulin to Glyburide," *Diabete. Metab.* 17:232-234, Masson (1991).

International Search Report for International Application No. PCT/MX02/00003, mailed on Jan. 30, 2003, European Patent Office, Rijswijk, Netherlands.

International Preliminary Examination Report for International Application No. PCT/MX02/00003, completed on Apr. 28, 2004, European Patent Office, Munich, Germany.

Shimpi, R.D., et al., "Comparison of effect of metformin in combination with glimepiride and glibenclamide on glycaemic control in patient with type 2 diabetes mellitus," *Int. J PharmTech Res.* 1:50-61, Sphinx Knowledge House (Jan.-Mar. 2009).

\* cited by examiner

PHARMACEUTICAL COMPOSITION CONTAINING GLIMEPIRIDE AND METFORMIN HYDROCHLORIDE

FIELD OF THE INVENTION

This invention consists of providing a therapeutic combination consisting of the sulfonylurea glimepiride and the biguanide metformin, both oral hypoglycemics, which, when combined, produce not only an additive effect but also a synergistic effect and therefore greater effectiveness in controlling blood glucose levels in patients with type 2 diabetes.

BACKGROUND

The use of sulfonylureas in treating type 2 diabetes is fully established as an effective means of controlling hypoglycemia. At the molecular level, sulfonylureas act on the receptor in β pancreatic cells known as SUR, which, when it is activated, closes an ATP dependent potassium channel, which in turn causes a reduction in potassium intake and in consequence depolarization of the membrane. This in turn causes an increase in the flow of calcium toward the cell's interior, activating the cytoskeleton, which causes translocation of secretory granules, thereby releasing insulin by exocytosis.

Another treatment whose use has spread recently is with the biguanide metformin, which acts effectively not only to control hypoglycemia, but also in its prevention. Metformin has a different mechanism of action from sulfonylureas, increasing insulin sensitivity in hepatic and peripheral tissue (mainly muscular tissues). Metformin inhibits gluconeogenesis and hepatic glycogenolysis. At the cellular level, heightened insulin sensitivity is explained by the increased activity it induces in the tyrosin kinase post-receptor and the resulting increase in the number and activity of GLUT4 transporters.

However, around 75% of type 2 diabetes patients treated with sulfonylureas do not succeed in bringing their glucose level to the desired values, and need to complement their treatment with a second oral agent. Also, most patients with single drug treatment using sulfonylureas after a certain number of years require an additional drug that contributes to their control therapy in order to achieve a suitable level of glycemic control. This loss of effectiveness is attributed to various causes, which are not yet well established, such as the supposition that gradual deterioration of the pancreas renders it unable to maintain an exacerbated insulin excretion rate for a long period of time due to constant, long-term stimulation caused by sulfonylurea therapy. However, contrary to this explanation, metformin therapy, which does not act by over stimulating β cells, also presents lack of response after prolonged use, which would be contradictory to the explanation given for the lack of response of sulfonylureas.

On the other hand it has been found that combining sulfonylurea and metformin therapy is more effective than monotherapy with either of the two medications. Thus, it has been fully proven that the hypoglycemic action of metformin is completely additional to that of sulfonylureas (de Fronzo, R. A. and Goodman, A. M. Yn, *England J. Med.* 333:541 (1995)).

Its also has been reported that when monotherapy with sulfonylureas does not achieve the desired levels it should not be discontinued and replaced by metformin monotherapy, as this will not lower glucose levels in plasma below the values observed with sulfonylurea monotherapy (Rosenstock, J. et al., *Diabetes Care* 19:1994 (1996); (Gasber, A. J., et al., *Amer. J. Med.* 103:491 (1997)).

It is generally recognized that, because diabetes mellitus is a progressive disease, patients with good initial response to oral agents will eventually require a second medication to achieve the desired glycemic control. As we have mentioned, adding metformin to sulfonylurea therapy or vice-versa produces an additive response, not only to the reduction in glucose, but also to the reduction in lipids (Hermann, L. S., et al., *Diabetes Care,* 17:1100 (1994)).

There are several reports on the combined use of the sulfonylurea glibenclamide with the biguanide metformin. See, e.g., WO 97/17975; Vigneri et al., *Diabetes and Metabolism,* 17:232-234 (1991); Higginbotham et al., *Med. J. Austr.,* 154-156 (1979); U.S. Pat. No. 6,303,146; and WO 01/32,158.

Furthermore, there are several references on the combined use of the sulfonylurea glipizide with metformin. See, e.g., Cefalu et al., *Diabetes,* 45 (Supl. 2):201A (1996); Croase et al., *Circulation,* 94 Supl 1508 (1996); and Cefalu et al., *Diabetology,* 39 (Supl. 1): A231 (1996).

It has been reported that there are no great differences in efficacy among various sulfonylureas (R. A. De Fronzo, *Annals of Internal Medicine,* 131:281-303 (1999)); S. Dagogo-Jack, et al., *Archives Internal Medicine,* 157:1802-1817 (1997); A. J. Scheen et al., *Drugs* 55:225-236 (1998); R. Bressler et al., *Archives Internal Medicine,* 157:836-848 (1997). Other reports indicate that glimepiride shows a potency two times higher than that of glibenclamide (R. Groomis et al., *Endocrinology,* 13:117-121 (2000)). Moreover, in contrast to glibenclamide, chronic treatment of type 2 diabetic patients with glimepiride will not impair the vasodilator function of $K_{ATP}$ opening in vivo (E. J. Abbink et al., *Diabetic Medicine,* 19:136-143 (2002). Furthermore, a lower incidence of severe hypoglycemia was reported in type 2 diabetic patients treated with glimepiride versus glibenclamide (A. Holstein et al. *Diabetologia,* 157:A40 (2000). Finally, Kramer et al., *Biochimica et Biphysica Acta* 1191: 276-290 (1999)), reported that glimepiride acts on a different receptor site on the β-cell than does glibenclamide, and that glimepiride interacts with the β-cell receptor for less time. Unlike glibenclamide, glimepiride seems to work in part by enhancing both the sensitivity and reponsiveness of peripheral tissue to insuline (J. Sato et al. *Excerpta Medica,* 341-348 (1994), G. E. Sonnenberg et al., *Annales Pharmaceuticals,* 31:671-676 (1997)).

DESCRIPTION OF THE INVENTION

Combined glimepiride and metformin have been suggested previously in the literature (G. Charpentier et al. *Diabetic Medicine* 18:828-834 (2001)). However, very little data is provided on its advantages or appropriate dosages. The prescribing information for the drug Amaryl (which active ingredient is glimepiride) warns of its supposed risk of hypoglycemia due to concomitant use metformin (Physicians Desk Reference, 54 Edition, 2000, page 1349). Thus, the current state of the art does not suggest the development and use of a pharmaceutical composition combining glimepiride and metformin, which in the present invention has been found to offer unexpected advantages.

With the present invention we have performed clinical studies which indicate that a pharmaceutical composition comprising a combination of glimepiride and metformin in determined fixed ratios decreased the glycosylated haemoglobin ($HbA_{1c}$) in a synergistic way compared to using glimepiride and metformin separately (Gonzalez-Ortiz et al., *Rev. Inv. Clin.* 56, in press, 2004). That is, the combined use of both drugs in certain ratios displays a synergistic effect on the efficacy greater than the additive efficacy of glimepiride and metformin used separately. This synergistic effect, beside being manifested in the control of glycosylated haemoglobin (HbA$_{1c}$), also controls fasting blood glucose (FBG) and post-prandial blood glucose (PPBG).

WO 00/40233 describes a pharmaceutical composition of glimepiride and metformin. However, this composition is designed to deliver an initial concentration of glimepiride, and later a delayed delivery of metformin. By this way of delivering both components it is not possible to maintain an appropriate bioavailability of the combined use of glimepiride and metformin to achieve a synergistic effect.

In the clinical studies performed concerning the present invention, it has been found that in order to obtain a pharmaceutical synergy, the ratio between metformin/glimepiride must be maintained in the range between about 500/1 to about 500/2 and using the appropriate dosage of metformin/glimepiride of 500/1, 500/2, 1000/2, 1000/4 (mg/mg), preferably 1000/2 mg/mg using a single dosage in a single tablet containing both drugs with 250 ml of water. After 10 hr of fasting in 16 healthy volunteers, 8 men and 8 women, the plasma concentrations of glimepiride was $C_{max}$=194.43+/−63.51 ng/ml and for metformin 2245.16+/−580.91 ng/ml in a time of 1.98+/1−0.59 hrs and 1.56+/−0.56 hrs, respectively. The half life of glimepiride was 3.73+/−1.28 hours, and of metformin was 2.62+/−0.33 hours. Using these conditions and the mentioned ratio of glimepiride and metformin a synergistic control was observed in the glycosylated hemoglobin (HbA$_{1c}$), in the control of fasting blood glucose (FBG), and in the post-prandial blood glucose (PPBG).

The great inconvenience of the pharmaceutical composition described in the above mentioned patent WO 00/40233 A is that there is an initial and total delivery of glimepiride followed by a delayed delivery of metformin. Taking into account the short half life of glimepiride (around 3.73 hours), when the metformin starts delivering the glimepiride concentration in the blood will be falling such that there will be a variable proportion of both drugs in the blood as a function of time. After a longer period of time, the glimepiride will be cleared from the blood and only the delayed metformin will persist. The net effect is a sequential medication of glimepiride alone followed by a combined medication of glimepiride and metformin with variable concentrations in the blood, followed by the supply of metformin alone. With this type of bioavailability, it will be impossible to observe any synergistic effect of the combination of both drugs.

The purpose of this invention is to provide a pharmaceutical composition consisting of glimepiride and metformin as its hydrocloride salt, or any other salt, and oral hypoglycemic therapy combining glimepiride and metformin in a single fixed ratio that is more effective and just as safe as monotherapy with the same compounds in patients with uncontrolled type 2 diabetes mellitus.

To demonstrate the above, a random double blind clinical study was conducted with a universe of 30 patients with uncontrolled type 2 diabetes mellitus who receive monotherapy with sulfonylureas or biguanides per group.

Criteria for inclusion were as follows:
1. Body mass index=27 kg/m$^2$;
2. Age 40 to 65;
3. Capacity for deglutition; and
4 Voluntary consent Criteria for exclusion were as follows:
1. Pregnancy;
2. Insulin treatment; and
3. Personal background of systemic diseases such as:
   a) Cardiac insufficiency; and
   b) Hepatic or chronic hepatopathic insufficiency.
4 Background of significant chronic complications with type 2 diabetes mellitus:
   a) Renal insufficiency;
   b) Ischemic cardiopathy;
   c) Cerebral vascular disease; and
   d) Visceral neuropathy.
5. Background of short-term terminal diseases, such as:
   a) Cancer; and
   b) HIV
6. Therapy with medications that present pharmacological interaction with glimepiride or metformin, such as acetozolamide, nicotinic acid, para-aminosalicylic acid, non-steroidal anti-inflammatory analgesics, histamine antagonists 2, barbiturates, cyclophosamide, clonidine, cloranphenicol, cumarinics, disopyramide, epinephrine, estatines, fenfluramine, phenotiacine, fibrates, fluoxetine, guanitidine, steroid hormones, iphosamide, monoaminoxidase inhibitors, laxatives, miconazole, quinolones, reserpine, rifamicine, sulfamides, and tetracycline.
7. Known intolerance or allergies to sulfonylureas or biguanides.

Criteria for exclusion from the therapy, but not from the statistical analysis:
1. Presence of severe hypoglycemia at the maximum dosages used in the study;
2. Presence of severe hypoglycemia at the minimum dosages used in the study;
3. Presence of intolerable undesirable effects with any of the medications used in the study;
4. Failure to follow the medical treatment indicated;
5. Failure to attend scheduled visits;
6. Intercurrent illnesses or accidents that warrant hospitalization;
7. Administration during the study of medications with pharmacological interaction with metformin or glimepiride; and
8. Voluntary withdrawal from the study.

The variables studied were as follows:
Dependent variables:
   a) Glycemia between meals;
   b) Glucosylated hemoglobin;
   c) β cell function;
   d) Insulin resistance; and
   e) Metabolic profile.
Independent variable:
   a) Hypoglycemic therapy.
Intervening variables:
   a) Age;
   b) Sex;
   c) Body mass index; and
   d) Evolution of diabetes.

DEFINITIONS

Levels of glycemia between meals>139 mg/dL are defined as type 2 diabetes mellitus.

Severe hypoglycemia: Glycemia between meals>260 mg/dL.

Severe hypoglycemia: Glycemia<60 mg/dL.

Non-adherence: Medication absorption<80%.

Absence: Missed appointment on >1 occasion.

PROCEDURE

Identification, clinical history and selection of participants:

Clinical measurements and basal measurement of glycemia between meals, glucosylated hemoglobin, total cholesterol, cholesterol of high density lipoproteins, triglycerides, creatinine, uric acid, glutemic-oxaloacetic transaminase, glutemic-pyruvic transaminase, lactic dehydrogenase, alkaline and insulin phosphatase.

Random assignment of patients to each group and pharmacological intervention in accordance with concentration of basal glycemia:

| a) Glimepiride (2 mg tablets) | | |
|---|---|---|
| Glycemia 140-180 mg/dl | 1 mg | ½ tablet |
| Glycemia 181-220 mg/dl | 2 mg | 1 tablet |
| Glycemia 221-260 mg/dl | 4 mg | 2 tablets |
| b) Metformin (1000 mg tablets) | | |
| Glycemia 140-180 mg/dl | 500 mg | ½ tablet |
| Glycemia 181-220 mg/dl | 1000 mg | 1 tablet |
| Glycemia 221-260 mg/dl | 2000 mg | 2 tablets |
| c) Glimepiride/Metfonnin (2/1000 mg tablets) | | |
| 140-180 mg/dl | 1/500 mg | ½ tablet |

Clinical evaluation 30 and 60 days after beginning the study, measuring glycemia between meals and lactic dehydroginase.

Final clinical evaluations 90 days after the study begins, measuring glycemia between meals, glucosylated hemoglobin, total cholesterol, high density lipoprotein cholesterol, triglyceride, creatinine, uric acid, glutemic-oxaloacetic transaminase, glutemic-pyruvic transaminase, lactic dehydrogenase, alkaline and insulin phosphatase.

Undesirable effects were reported on a special record sheet, specifying each of the clinical manifestations considered probable, possible or directly related to the use of the drugs ingested.

The results obtained show that combined metformin and glimepiride therapy was more effective in controlling glucosylated hemoglobin levels, post-prandial blood glucose levels and blood glucose levels between meals than single-drug treatment with glimepiride or metformin alone. The results obtained are shown below:

| | Combination | glimepiride | metformin |
|---|---|---|---|
| Glucosylated hemoglobin $HbA_{1c}$ | −0.70 | +0.25 | +0.06 |
| Blood glucose between meals | −1.77 | +0.68 | +0.75 |
| Post-prandial blood glucose | −2.7 | +0.99 | +1.08 |

What is extraordinary about the values obtained is that monotherapy with either glimepiride or metformin has a similar effect in raising glucose levels, while treatment with the combination clearly shows a beneficial effect, which highlights its importance.

The previous combinations used in the clinical study can be illustrated by means of the following examples:

EXAMPLE 1

A pharmaceutical composition is prepared consisting of 500 mg of metformin hydrochloride and 1 mg of glimepiride, adding the following excipients:

| Microcrystalline Cellulose PH 101 | 39.20 mg |
|---|---|
| Coloidal Silica Dioxide | 1.80 mg |
| Povidone K-90 | 18.00 mg |
| Croscarmelose Sodium | 12.00 mg |
| Magnesium stereate | 3.00 mg |
| Clear Opadray YS-1-7006 | 5.00 mg |
| Purified water | 0.204 mg |

This pharmaceutical composition was used for the aforementioned clinical tests.

EXAMPLE 2

A pharmaceutical composition is prepared consisting of 500 mg of metformin hydrochloride and 2 mg of glimepiride, adding the following excipients:

| Microcrystalline Cellulose PH 101 | 38.20 mg |
|---|---|
| Coloidal Silica Dioxide | 1.80 mg |
| Povidone K-90 | 18.00 mg |
| Croscarinelose Sodium | 12.00 mg |
| Magnesium stereate | 3.00 mg |
| Clear Opadray YS-1-7006 | 5.00 mg |
| Purified water | 0.204 mg |

This pharmaceutical composition was used for the aforementioned clinical tests.

EXAMPLE 3

A pharmaceutical composition is prepared consisting of 1000 mg of metformin hydrochloride and 2 mg of glimepiride, adding the following excipients:

| Microcrystalline Cellulose PH 101 | 78.40 mg |
|---|---|
| Coloidal Silica Dioxide | 3.60 mg |
| Povidone K-90 | 36.00 mg |
| Croscarmelose Sodium | 24.00 mg |
| Magnesium stereate | 6.00 mg |
| Clear Opadray YS-1-7006 | 6.25 mg |
| Purified water | 0.345 ml |

This pharmaceutical composition was used for the aforementioned clinical tests.

EXAMPLE 4

A pharmaceutical composition is prepared consisting of 1000 mg of metformin hydrochloride and 4 mg of glimepiride, adding the following excipients:

| Microcrystalline Cellulose PH 101 | 78.40 mg |
|---|---|
| Coloidal Silica Dioxide | 3.60 mg |
| Povidone K-90 | 36.00 mg |
| Croscarmelose Sodium | 24.00 mg |
| Magnesium stereate | 6.00 mg |
| Clear Opadray YS-1-7006 | 6.25 mg |
| Purified water | 0.345 ml |

This pharmaceutical composition was used for the aforementioned clinical tests.

The invention claimed is:

1. A solid pharmaceutical composition, comprising a synergistic combination of glimepiride and metformin hydrochloride, wherein the weight ratio of glimepiride and metformin hydrochloride is about 1/500, and wherein the combination of glimepiride and metformin hydrochloride reduces blood glucose levels in a patient with type 2 diabetes greater than either glimepiride or metformin hydrochloride alone, wherein the composition further comprises 18 mg to 36 mg of povidone, 3 mg to 6 mg of magnesium stearate, and 1.8 mg to 3.6 mg of colloidal silicon dioxide.

2. The solid pharmaceutical composition according to claim 1, comprising 500 mg metformin hydrochloride and 1 mg glimepiride.

3. The solid pharmaceutical composition according to claim 1, comprising 1000 mg metformin hydrochloride and 2 mg glimepiride.

4. A method of controlling blood glucose levels in a patient with type 2 diabetes, comprising administering the composition of claim 1 to said patient.

5. The method according to claim 4, comprising administering a composition wherein glimepiride and metformin hydrochloride are present in amounts of 1 mg glimepiride and 500 mg metformin hydrochloride or 2 mg glimepiride and 1000 mg metformin hydrochloride.

6. The method according to claim 4, comprising administering a composition wherein glimepiride and metformin hydrochloride are present in amounts of 1 mg glimepiride and 500 mg metformin hydrochloride.

7. The method according to claim 4, comprising administering a composition wherein glimepiride and metformin hydrochloride are present in amounts of 2 mg glimepiride and 1000 mg metformin hydrochloride.

8. The solid pharmaceutical composition according to claim 1, wherein the combination of glimepiride and metformin hydrochloride reduces blood glucose levels in a patient with type 2 diabetes greater than the additive effect of glimepiride and metformin hydrochloride alone.

9. The method according to claim 4, wherein the combination of glimepiride and metformin hydrochloride reduces blood glucose levels in a patient with type 2 diabetes greater than the additive effect of glimepiride and metformin hydrochloride alone.

10. The solid pharmaceutical composition according to claim 1, wherein the combination of glimepiride and metformin hydrochloride reduces glycosylated hemoglobin levels in a patient with type 2 diabetes greater than either glimepiride or metformin hydrochloride alone.

11. The method according to claim 4, wherein the combination of glimepiride and metformin hydrochloride reduces glycosylated hemoglobin levels in a patient with type 2 diabetes greater than either glimepiride or metformin hydrochloride alone.

12. The solid pharmaceutical composition according to claim 10, wherein the combination of glimepiride and metformin hydrochloride reduces glycosylated hemoglobin levels in a patient with type 2 diabetes greater than the additive effect of glimepiride and metformin hydrochloride alone.

13. The method according to claim 11, wherein the combination of glimepiride and metformin hydrochloride reduces glycosylated hemoglobin levels in a patient with type 2 diabetes greater than the additive effect of glimepiride and metformin hydrochloride alone.

14. The solid pharmaceutical composition according to claim 1, further comprising microcrystalline cellulose and croscarmellose sodium.

15. The solid pharmaceutical composition according to claim 14, further comprising opadry clear.

16. The solid pharmaceutical composition according to claim 1, further comprising 18 mg of povidone, 3 mg of magnesium stearate, and 1.8 mg of colloidal silicon dioxide.

17. The solid pharmaceutical composition according to claim 1, further comprising 36 mg of povidone, 6 mg of magnesium stearate, and 3.6 mg of colloidal silicon dioxide.

18. The solid pharmaceutical composition according to claim 2, further comprising 18 mg of povidone, 3 mg of magnesium stearate, and 1.8 mg of colloidal silicon dioxide.

19. The solid pharmaceutical composition according to claim 3, further comprising 36 mg of povidone, 6 mg of magnesium stearate, and 3.6 mg of colloidal silicon dioxide.

* * * * *